(12) United States Patent
Chuang

(10) Patent No.: US 7,662,268 B2
(45) Date of Patent: Feb. 16, 2010

(54) METHOD AND SYSTEM FOR MEASURING THE ZETA POTENTIAL OF THE CYLINDER'S OUTER SURFACE

(75) Inventor: Ching-Jung Chuang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 561 days.

(21) Appl. No.: 11/531,256

(22) Filed: Sep. 12, 2006

(65) Prior Publication Data
US 2008/0072685 A1    Mar. 27, 2008

(51) Int. Cl.
*B01D 17/06* (2006.01)
*B01D 57/02* (2006.01)

(52) U.S. Cl. .............. 204/556; 204/450; 204/451; 204/549; 204/554; 204/555; 204/409; 204/600; 204/601; 204/602; 204/645; 204/660; 204/661; 204/670; 204/671

(58) Field of Classification Search .............. 204/450, 204/451, 549, 554, 555, 556, 409, 600, 601, 204/602, 645, 660, 661, 670, 671
See application file for complete search history.

(56) References Cited

U.S. PATENT DOCUMENTS

| | | | |
|---|---|---|---|
| 6,766,817 B2 | 7/2004 | da Silva | |
| 6,918,404 B2 | 7/2005 | Dias da Silva | |
| 7,066,586 B2 | 6/2006 | da Silva | |
| 2002/0022100 A1* | 2/2002 | Gord et al. | 428/36.9 |
| 2003/0024817 A1* | 2/2003 | Chun et al. | 204/549 |
| 2005/0178702 A1* | 8/2005 | Chuang et al. | 210/85 |
| 2009/0251128 A1* | 10/2009 | Chuang et al. | 324/76.11 |

\* cited by examiner

*Primary Examiner*—Bruce F Bell
(74) *Attorney, Agent, or Firm*—WPAT., P.C.; Justin King

(57) ABSTRACT

The present invention discloses a method for measuring the zeta potential at the cylinder's outer surface. In the measuring cell, the cylinder is held coaxially inside a reference tube and a given solution is forced to flow through the annular flow channel between the cylinder and the reference tube. The streaming potential induced by the flow forced with a hydraulic pressure drop is measured to determine the zeta potential, $\zeta_m$, of the cylinder's outer surface by using the following Equation, $$\frac{E}{\Delta P} = -\frac{D}{\mu k}\left(\frac{\zeta_m + \zeta_{ref}}{2}\right)F$$

where D is the permittivity, $\zeta_{ref}$ is the zeta potential of the reference tube, $\mu$ is the viscosity of the solution, k is the electric conductivity of the solution, and F is a correction factor for the electrokinetic model. Moreover, this invention also discloses a system for measuring the zeta potential of the cylinder's outer surface.

17 Claims, 2 Drawing Sheets

METHOD AND SYSTEM FOR MEASURING THE ZETA POTENTIAL OF THE CYLINDER'S OUTER SURFACE

BACKGROUND OF THE INVENTION

1. Field of the Invention

The present invention is generally related to a method for measuring zeta potential, and more particularly to a method for measuring the zeta potential of the cylinder's outer surface and measurement system thereof.

2. Description of the Prior Art

Membrane technology was focused on flat membrane during early development while the development of tubular membrane was started around in 1960s from hollow-fiber membrane used in gas separation made by DuPont. Because hollow-fiber membrane has advantages of high specific surface area per unit volume and self-supporting property, it is extensively applied in gas separation, reverse osmosis, hemodialysis, ultrafiltration, microfiltration, and so forth.

Membrane electric charge generally plays an important role in determining its separation performance. Currently, the measurement of zeta potential of membrane focuses on flat membranes. In practice, tubular membrane has been extensively applied in the industry but there is no method provided to measure the zeta potential of the outer surface of tubular membrane. Thus, generally the industry or researchers accept the information supplied by the manufacturer to qualitatively determine the charge property of the membrane. However, membrane electric charges are affected by not only material of the membrane but also the property of solution, such as pH value and ionic intensity. Since there is no effective method provided to quantitatively characterize the charge of the outer surface of cylindrical type objects, therefore it is required to develop a method and measurement system for measuring zeta potential of the cylinder's outer surface, especially the zeta potential of the outer surface of cylindrical membranes. According to the zeta potential, filtration conditions designed to reduce the membrane fouling can be provided and thus the filtration capacity and the selectivity in separation can be enhanced.

SUMMARY OF THE INVENTION

According to the above background, the present invention provides method and system to measure the zeta potential of the cylinder's outer surface to fulfill the requirements of this industry.

One object of the present invention is to measure the zeta potential of the cylinder's outer surface by annular pipe design. At first, a reference tube is solely provided. The streaming potential due to solution flow in the single tube (straight flow channel) is used to obtain the zeta potential at the inner wall of the reference tube. After that, the cylinder measured is placed coaxially inside the reference tube and solution is forced by pressure to flow through the annular flow channel between the cylinder and the reference tube. The streaming potential between the two ends of the annular flow channel is measured. Finally, the zeta potential of the cylinder's outer surface is determined by using an electrokinetic relationship between the streaming potential and the zeta potentials of the reference tube and the cylinder. This method is easy to operate and has simple system installation. Thus, the present invention does have the economic advantages for industrial applications.

Accordingly, the present invention discloses a method for measuring the zeta potential of the cylinder's outer surface. A cylinder having a first radius and a reference tube having a second radius are provided, wherein the first radius is smaller than the second radius. At first, the streaming potential due to solution flow in the single tube (straight flow channel) is used to obtain the zeta potential, $\zeta_{ref}$, at the inner wall of the reference tube. Then, the cylinder is placed coaxially inside the reference tube. After that, the solution is forced by a pressure difference $\Delta P$ to flow through the annular flow channel and then the streaming potential difference E between the two ends of the annular flow channel is measured by electrodes. Finally, the zeta potential $\zeta_m$ of the cylinder's outer surface is determined by the electrokinetic relationship as:

$$\frac{E}{\Delta P} = -\frac{D}{\mu k}\left(\frac{\zeta_m + \zeta_{ref}}{2}\right) F$$

where D is the permittivity, k is the electric conductivity of solution, μ is the viscosity of the solution, and F is a correction factor for the electrokinetic model. Furthermore, this invention also discloses a system for measuring the zeta potential of the cylinder's outer surface.

DESCRIPTION OF THE PREFERRED EMBODIMENTS

What is probed into the invention is method and system to measure the zeta potential of the cylinder's outer surface. Detail descriptions of the measuring procedures and system will be provided in the following in order to make the invention thoroughly understood. Obviously, the application of the invention is not confined to specific details familiar to those who are skilled in the art. On the other hand, the common process and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
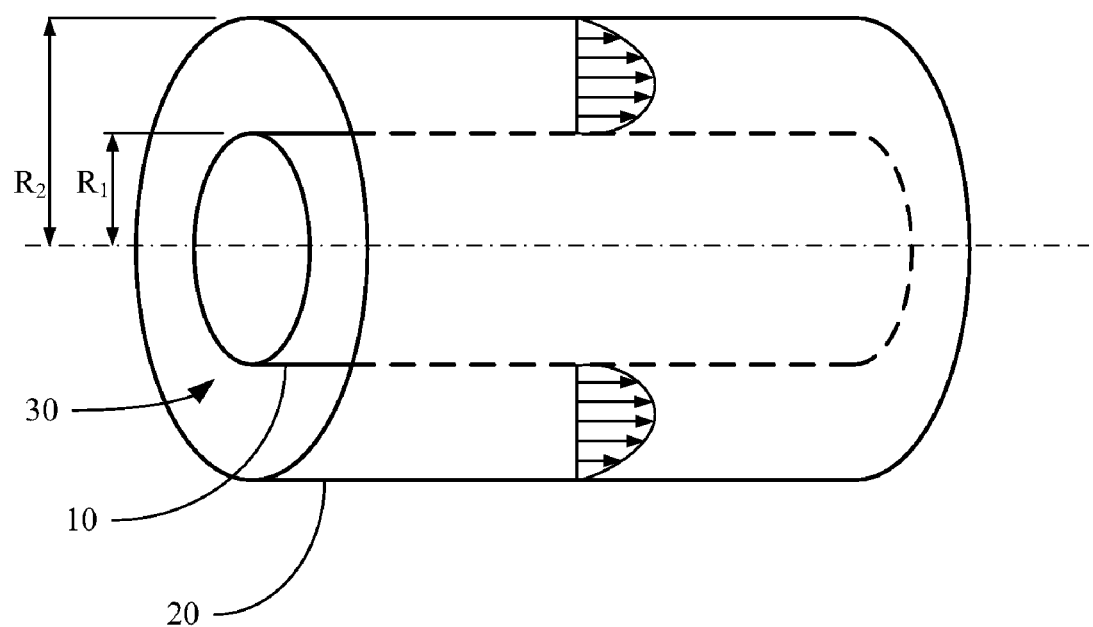
FIG. 1 is a schematic diagram illustrating the relative positions among the cylinder, reference tube, and annular flow channel according to a first embodiment of the present invention.

Referring to FIG. 1, a first embodiment of the present invention discloses a method for measuring the zeta potential of the cylinder's outer surface. At first, a cylinder 10 having a first radius $R_1$ and a reference tube 20 having a second radius $R_2$ are provided. The first radius $R_1$ is smaller than the second radius $R_2$. There is channel between the cylinder 10 and the reference tube 20 to form a annular flow channel 30. In addition, the cylinder 10 is coaxial with the reference tube 20. Next, a solution is introduced to the annular flow channel 30. After that, the solution is forced by a pressure difference $\Delta P$ to flow through the annular flow channel 30, wherein the flow direction of the solution is parallel to the axial direction of the reference tube 20. The net electric charges in the electric double layer on the two walls move along with the flow so as to generate streaming potential. A measuring process is performed to measure the streaming potential difference $\overline{E}$ between the two ends of the annular flow channel 30 by electrodes. Finally, the zeta potential $\xi_m$ of the cylinder's outer surface is determined using the electrokinetic relationship as:

$$\frac{\overline{E}}{\Delta P} = -\frac{D}{\mu k}\left(\frac{\zeta_m + \zeta_{ref}}{2}\right)F$$

where D is the permittivity [$D = \in_r \in_0$, where $\in_r$ is relative dielectric constant and $\in_r$ is dielectric constant in vacuum ($=8.85 \times 10^{-12} C^2 J^{-1} m^{-1}$)], $\zeta_{ref}$ is the zeta potential at the inner wall of the reference tube, $\mu$ is the viscosity of the solution, k is the electric conductivity of the solution, and F is a correction factor for the electrokinetic model.

In this embodiment, the cylinder 10 comprises one selected from the group consisting of the following: tubular membrane, capillary membrane, hollow fiber, fiber, and wire. In addition, if the cylinder is porous, the two ends of the cylinder are sealed to prevent the solution from flowing inside the cylinder to affect the measurement result. Moreover, the inner wall of the reference tube 20 is substantially smooth to prevent the solution from abnormal disturbance to affect the measurement result. Besides, the electric conductivity and the pH value of the solution can be measured in advance or by the measuring process.

In this embodiment, the correction factor F has a general expression as the following:

$$F = \frac{2}{\left(\frac{\zeta_m}{\zeta_{ref}}\right)+1} + \frac{1-\frac{\zeta_{ref}}{\zeta_m}}{1+\frac{\zeta_{ref}}{\zeta_m}} \times \frac{b^2-1-2b^2 \cdot \ln b}{\ln b \cdot (1-b^2)} -$$

$$\frac{4 \cdot [I_1(\lambda) - b \cdot I_1(\lambda b)]}{\lambda \cdot (1-b^2) \cdot \left(1+\frac{\zeta_{ref}}{\zeta_m}\right)} \times \left[\frac{K_0(\lambda) - \frac{\zeta_{ref}}{\zeta_m} \cdot K_0(\lambda b)}{I_0(\lambda b) \cdot K_0(\lambda) - K_0(\lambda b) \cdot I_0(\lambda)}\right] -$$

$$\frac{4 \cdot [b \cdot K_1(\lambda b) - K_1(\lambda)]}{\lambda \cdot (1-b^2) \cdot \left(1+\frac{\zeta_{ref}}{\zeta_m}\right)} \times \left[\frac{\frac{\zeta_{ref}}{\zeta_m} \cdot I_0(\lambda b) - I_0(\lambda)}{I_0(\lambda b) \cdot K_0(\lambda) - K_0(\lambda b) \cdot I_0(\lambda)}\right]$$

$$\text{where } b = \frac{R_1}{R_2}, \lambda = \frac{R_2}{\frac{1}{\kappa}},$$

$\kappa$ (reciprocal Debye length) can be treated as the reciprocal of the thickness of the electric double layer, $I_0$ and $I_1$ are the zero-order and first order modified Bessel functions of first kind, respectively, and, $K_0$ and $K_1$ are the zero-order and first order modified Bessel functions of second kind, respectively.

Figure 2:
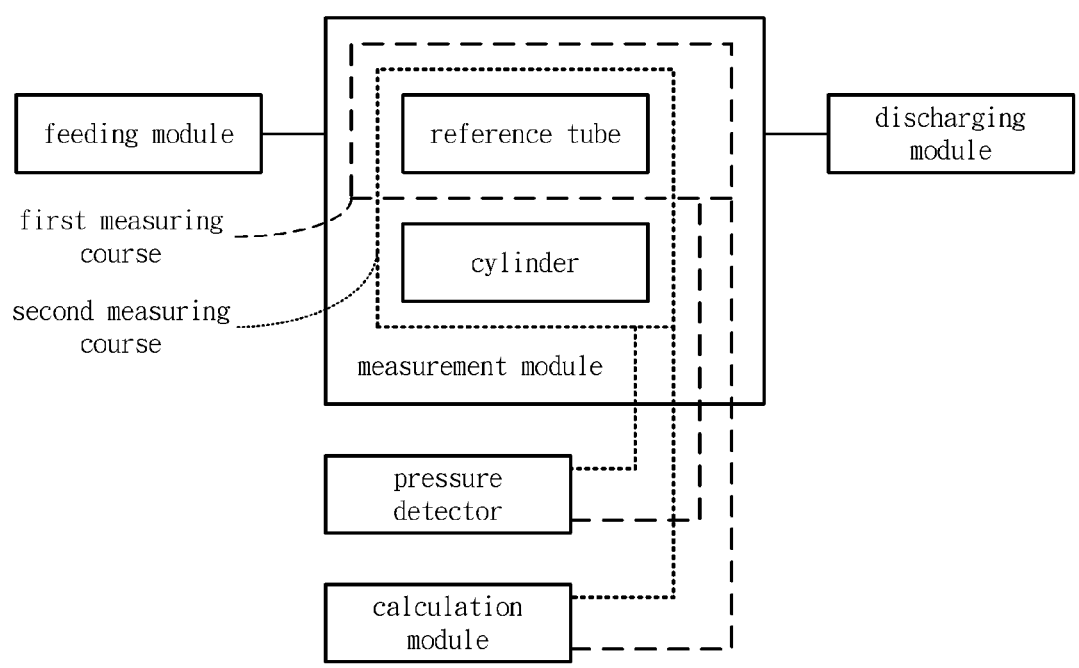
FIG. 2 is a schematic diagram illustrating the measurement system for measuring the streaming potential according to a second embodiment of the present invention.

Referring to FIG. 2, a second embodiment of the present invention discloses a measurement system for measuring the zeta potential of the cylinder's outer surface. The system comprises: a feeding module; a measurement module having a reference tube; a discharging module; at least one pressure detector; and a calculation module. The measurement module receives a solution from the feeding module, the solution is forced to flow through the inner side of the reference tube, which forms a straight flow channel, and then the solution is discharged to a discharging module so as to form a first measuring course. Thus, the measurement module generates a first potential difference signal via the first measuring course. Besides, the cylinder and the reference tube are assembled to form a second measuring course. The radius of the cylinder is smaller than that of the reference tube and the cylinder is coaxial with the reference tube. The solution received by the measurement module is forced to flow through the annular flow channel between the cylinder and the reference tube, and is discharged to the discharging module so as to form the second measuring course. The measurement module generates a second potential difference signal via the second measuring course.

The measurement module further comprises a first detector for measuring the potential of the solution at the inlet of the flow channel, and a second detector for measuring the potential of the solution at the outlet of the flow channel. In one case, the first detector and the second detector carry out detection in the first measuring course, so as to generate the first potential difference signal. In another case, the first detector and the second detector carry out detection in the second measuring course, so as to generate the second potential difference signal.

In this embodiment, the pressure detector is to measure the pressure difference between the two ends of the flow channel, so as to generate a pressure difference signal. Moreover, the calculation module comprises calculating the zeta potential $\xi_m$ of the cylinder's outer surface:

$$\frac{\overline{E}}{\Delta P} = -\frac{D}{\mu k}\left(\frac{\zeta_m + \zeta_{ref}}{2}\right)F$$

where D is the permittivity, $\zeta_{ref}$ is the zeta potential of the reference tube, $\mu$ is the viscosity of the solution, k is the electric conductivity of the solution, and F is a correction factor for the electrokinetic model (the general equation of F is described in the first embodiment). Additionally, the calculation module receives the first potential difference signal and the pressure difference signal to calculate the zeta potential of the inner surface of the reference tube. The calculation module receives the second potential difference signal and the pressure difference signal accompanying with the zeta potential of the inner surface of the reference tube to calculate the zeta potential of the outer surface of the cylinder. In addition, the measurement system further comprises an electric conductivity meter for measuring the electric conductivity of the solution and/or a pH meter for measuring the pH value of the solution.

In this embodiment, the cylinder comprises one selected from the group consisting of the following: tubular membrane, capillary membrane, hollow fiber, fiber, and wire. In addition, the two ends of the cylinders are sealed to prevent the solution from flowing inside the cylinder to affect the measurement result. Moreover, the inner wall of the reference tube is substantially smooth to prevent the solution from abnormal disturbance to affect the measurement result.

To sum up, the present invention discloses a method for measuring the zeta potential of the cylinder's outer surface. A cylinder having a first radius and a reference tube having a second radius are provided, wherein the first radius is smaller than the second radius. At first, the streaming potential due to solution flow in the single tube is used to obtain the zeta potential, $\zeta_{ref}$ at the inner wall of the reference tube. Then, the cylinder is placed coaxially inside the reference tube. After that, the solution is forced by a pressure difference ΔP to flow through the annular flow channel and then the streaming potential difference $\bar{E}$ between the two ends of the annular flow channel is measured by electrodes. Finally, the zeta potential $\xi_m$ of the cylinder's outer surface is calculated by:

$$\frac{\bar{E}}{\Delta P} = = -\frac{D}{\mu k}\left(\frac{\zeta_m + \zeta_{ref}}{2}\right)F$$

where D is the permittivity, $\zeta_{ref}$ is the zeta potential of the reference tube, μ is the viscosity of the solution, k is the electric conductivity of the solution, and F is a correction factor for the electrokinetic model. Furthermore, this invention also discloses a system for measuring the zeta potential of the cylinder's outer surface.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for measuring the zeta potential of the cylinder's outer surface, comprising:
    providing a cylinder having a first radius and a reference tube having a second radius, wherein the first radius is smaller than the second radius;
    the cylinder is placed coaxially inside the reference tube, and the channel existing between the cylinder and the reference tube forms a annular flow channel;
    introducing a solution to the annular flow channel;
    the solution is forced by a pressure difference ΔP to flow through the annular flow channel; and
    performing a measuring process to measure the streaming potential difference $\bar{E}$ between the two ends of the annular flow channel by electrodes, wherein the measuring process comprises calculating the zeta potential $\xi_m$ of the cylinder's outer surface from the following equation:

$$\frac{\bar{E}}{\Delta P} = = -\frac{D}{\mu k}\left(\frac{\zeta_m + \zeta_{ref}}{2}\right)F$$

where D is the permittivity, $\zeta_{ref}$ is the zeta potential of the reference tube, μ is the viscosity of the solution, k is the electric conductivity of the solution, and F is a correction factor for the electrokinetic model.

2. The method according to claim 1, wherein the cylinder comprises one selected from the group consisting of the following: tubular membrane, capillary membrane, hollow fiber, fiber, and wire.

3. The method according to claim 1, wherein the two ends of the cylinder are sealed.

4. The method according to claim 1, wherein the surface of the inner wall of the reference tube is substantially smooth.

5. The method according to claim 1, wherein the measuring process further comprises measuring the electric conductivity k of the solution.

6. The method according to claim 1, wherein the measuring process further comprises measuring the pH value of the solution.

7. The method according to claim 1, wherein the correction factor F has a general expression as the following:

$$F = \frac{2}{\left(\frac{\zeta_m}{\zeta_{ref}}\right)+1} + \frac{1-\frac{\zeta_{ref}}{\zeta_m}}{1+\frac{\zeta_{ref}}{\zeta_m}} \times \frac{b^2-1-2b^2\cdot \ln b}{\ln b \cdot (1-b^2)} -$$

$$\frac{4\cdot[I_1(\lambda)-b\cdot I_1(\lambda b)]}{\lambda\cdot(1-b^2)\cdot\left(1+\frac{\zeta_{ref}}{\zeta_m}\right)} \times \left[\frac{K_0(\lambda)-\frac{\zeta_{ref}}{\zeta_m}\cdot K_0(\lambda b)}{I_0(\lambda b)\cdot K_0(\lambda)-K_0(\lambda b)\cdot I_0(\lambda)}\right] -$$

$$\frac{4\cdot[b\cdot K_1(\lambda b)-K_1(\lambda)]}{\lambda\cdot(1-b^2)\cdot\left(1+\frac{\zeta_{ref}}{\zeta_m}\right)} \times \left[\frac{\frac{\zeta_{ref}}{\zeta_m}\cdot I_0(\lambda b)-I_0(\lambda)}{I_0(\lambda b)\cdot K_0(\lambda)-K_0(\lambda b)\cdot I_0(\lambda)}\right]$$

Where $b=R_1/R_2$, $$\lambda = \frac{R_2}{\frac{1}{\kappa}},$$

κ(reciprocal Debye length) can be treated as the reciprocal of the thickness of the electric double layer, $I_0$ and $I_1$ are the zero-order and first order modified Bessel functions of first kind, respectively, and, $K_0$ and $K_1$ are the zero-order and first order modified Bessel functions of second kind, respectively.

8. A system for measuring the zeta potential of the cylinder's outer surface, comprising:
    a feeding module;
    a measurement module comprising a reference tube, wherein the measurement module receives a solution from the feeding module, the solution is forced to flow through the inner side of the reference tube, which forms a straight flow channel, and then the solution is discharged to a discharging module so as to form a first measuring course, and thus the measurement module generates a first potential difference signal via the first measuring course, and besides, the cylinder and the reference tube are assembled to form a second measuring course, the radius of the cylinder is smaller than that of the reference tube, the cylinder is coaxial with the reference tube, the solution received by the measurement module is forced to flow through the annular flow channel between the cylinder and the reference tube, and is discharged to the discharging module so as to form the second measuring course, and the measurement module generates a second potential difference signal via the second measuring course;
    at least one pressure detector for measuring the pressure difference for solution flow from the inlet to the outlet of the flow channel to generate a pressure difference signal; and
    a calculation module, comprising calculating the zeta potential $\xi_m$ of the cylinder's outer surface:

$$\frac{\bar{E}}{\Delta P} = = -\frac{D}{\mu k}\left(\frac{\zeta_m + \zeta_{ref}}{2}\right)F$$

where D is the permittivity, $\zeta_{ref}$ is the zeta potential of the reference tube, μ is the viscosity of the solution, k is the electric conductivity of the solution, and F is a correction factor for the electrokinetic model, the calculation module receives the first potential difference signal and the pressure difference signal to calculate the zeta potential $\xi_{ref}$ of the inner surface of the reference tube, and the calculation module receives the second potential difference signal and the pressure difference signal accompanying with the zeta potential $\xi_{ref}$ of the inner surface of the reference tube to calculate the zeta potential $\xi_m$ of the outer surface of the cylinder.

9. The system according to claim 8, further comprises an electric conductivity meter for measuring the electric conductivity of the solution.

10. The system according to claim 8, further comprises a pH meter for measuring the pH value of the solution.

11. The system according to claim 8, wherein the cylinder comprises one selected from the group consisting of the following:
   tubular membrane, capillary membrane, hollow fiber, fiber, and wire.

12. The system according to claim 8, wherein the two ends of the cylinder are sealed.

13. The system according to claim 8, wherein the surface of the inner wall of the reference tube is substantially smooth.

14. The system according to claim 8, wherein the measurement module further comprises a first detector for measuring the potential of the solution at the inlet of the flow channel, and a second detector for measuring the potential of the solution at the outlet of the flow channel.

15. The system according to claim 14, wherein the first detector and the second detector carry out detection in the first measuring course, so as to generate the first potential difference signal.

16. The system according to claim 14, wherein the first detector and the second detector carry out detection in the second measuring course, so as to generate the second potential difference signal.

17. The system according to claim 8, wherein the correction factor F has a general equation as the following:

$$F = \frac{2}{\left(\frac{\zeta_m}{\zeta_{ref}}\right)+1} + \frac{1-\frac{\zeta_{ref}}{\zeta_m}}{1+\frac{\zeta_{ref}}{\zeta_m}} \times \frac{b^2-1-2b^2 \cdot \ln b}{\ln b \cdot (1-b^2)} -$$

$$\frac{4 \cdot [I_1(\lambda) - b \cdot I_1(\lambda b)]}{\lambda \cdot (1-b^2) \cdot \left(1+\frac{\zeta_{ref}}{\zeta_m}\right)} \times \left[\frac{K_0(\lambda) - \frac{\zeta_{ref}}{\zeta_m} \cdot K_0(\lambda b)}{I_0(\lambda b) \cdot K_0(\lambda) - K_0(\lambda b) \cdot I_0(\lambda)}\right] -$$

$$\frac{4 \cdot [b \cdot K_1(\lambda b) - K_1(\lambda)]}{\lambda \cdot (1-b^2) \cdot \left(1+\frac{\zeta_{ref}}{\zeta_m}\right)} \times \left[\frac{\frac{\zeta_{ref}}{\zeta_m} \cdot I_0(\lambda b) - I_0(\lambda)}{I_0(\lambda b) \cdot K_0(\lambda) - K_0(\lambda b) \cdot I_0(\lambda)}\right]$$

Where $b = R_1/R_2$, $$\lambda = \frac{R_2}{\frac{1}{\kappa}},$$

$\kappa$ (reciprocal Debye length) can be treated as the reciprocal of the thickness of the electric double layer, $I_0$ and $I_1$ are the zero-order and first order modified Bessel functions of first kind, respectively, and, $K_0$ and $K_1$ are the zero-order and first order modified Bessel functions of second kind, respectively.

* * * * *